(12) United States Patent
Kobayashi

(10) Patent No.: US 9,040,966 B2
(45) Date of Patent: May 26, 2015

(54) METHOD FOR PRODUCING ORGANIC TRANSISTOR, ORGANIC TRANSISTOR, METHOD FOR PRODUCING SEMICONDUCTOR DEVICE, SEMICONDUCTOR DEVICE, AND ELECTRONIC APPARATUS

(75) Inventor: Norihito Kobayashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/981,721

(22) PCT Filed: Feb. 23, 2012

(86) PCT No.: PCT/JP2012/054447
§ 371 (c)(1),
(2), (4) Date: Aug. 26, 2013

(87) PCT Pub. No.: WO2012/132674
PCT Pub. Date: Oct. 4, 2012

(65) Prior Publication Data
US 2013/0328036 A1 Dec. 12, 2013

(30) Foreign Application Priority Data
Mar. 30, 2011 (JP) ................................. 2011-075180

(51) Int. Cl.
H01L 35/24 (2006.01)
H01L 51/00 (2006.01)
C07D 493/06 (2006.01)
H01L 51/05 (2006.01)

(52) U.S. Cl.
CPC .......... *H01L 51/005* (2013.01); *H01L 51/0058* (2013.01); *H01L 51/0545* (2013.01); *C07D 493/06* (2013.01)

(58) Field of Classification Search
USPC .............................. 257/40, E51.041; 549/381
See application file for complete search history.

(56) References Cited

U.S. PATENT DOCUMENTS

2008/0277648 A1* 11/2008 Wakita ............................ 257/40
2009/0289248 A1* 11/2009 Kobayashi et al. ............. 257/40
2010/0013381 A1    1/2010 Stoessel et al.
2010/0019233 A1* 1/2010 Kawashima et al. ........... 257/40

FOREIGN PATENT DOCUMENTS

| JP | 2005-243822 | 9/2005 |
| JP | 2008-147225 | 6/2008 |
| JP | 2009-029746 | 2/2009 |
| JP | 2009/084584 | 7/2009 |
| JP | 2009-544743 A | 12/2009 |
| JP | 2010-006794 | 1/2010 |
| JP | 2010-028005 | 2/2010 |
| JP | 2010-028005 A | 2/2010 |
| JP | 2011-012001 A | 1/2011 |
| WO | WO-2009/084584 A1 | 7/2009 |

OTHER PUBLICATIONS

International Search Report; Application No. PCT/2012/054447; Filed: Feb. 23, 2012. Completion of International Search Report: Mar. 26, 2012. (Form PCT/ISA/210).
Written Opinion of the International Searching Authority; Application No. PCT/2012/054447; Filed: Feb. 23, 2012. Report Dated: Apr. 3, 2012. (Form PCT/ISA/237).
Norihito Kobayashi, et al., "Stable *peri*-Xanthenoxanthene Thin-Film Transistors with Efficient Carrier Injection," American Chemical Society, *Chem. Mater.*, vol. 21, No. 3, 2009, pp. 552-556.
Extended European Search Report mail Aug. 4, 2014 for corresponding European Application No. 12 764 834.3.
Japanese Office Action issued Feb. 24, 2015 for corresponding Japanese Application No. 2011-075180.

* cited by examiner

*Primary Examiner* — Phuc Dang
(74) *Attorney, Agent, or Firm* — Rader, Fishman & Grauer PLLC

(57) ABSTRACT

Provided is a method of producing an organic transistor, including collectively forming a gate insulating film and an organic semiconductor film by applying, onto a gate electrode, a solution including a polymer and at least one of compounds represented by General Formulas 1 to 4 and 5 to 7, a compound having a structure represented by General Formula 4, a compound having a structure represented by General Formula 5 or 6, and forming a source electrode and a drain electrode on the organic semiconductor film.

(1)

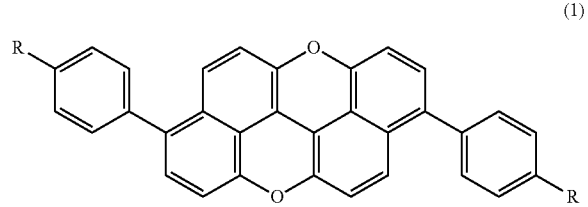

(2)

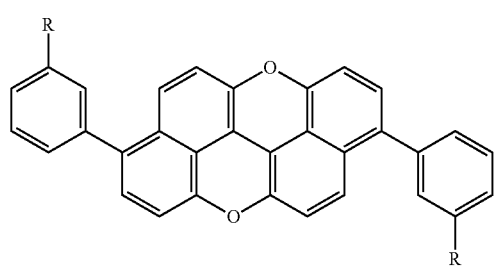

(3)

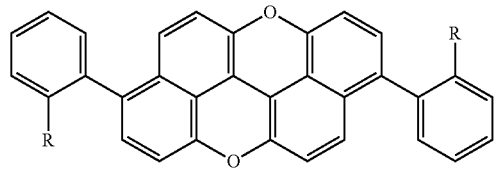

(where R is a linear or branched alkyl group)

(4)

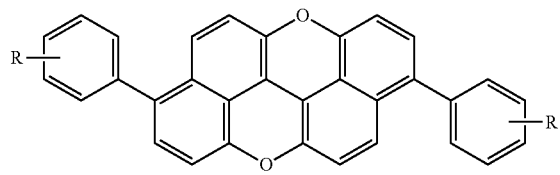

(where R is an alkyl group)

(5)

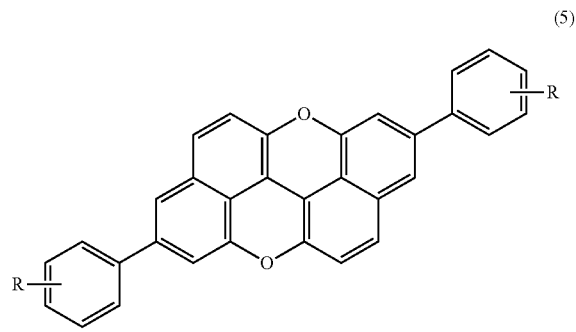

(6)

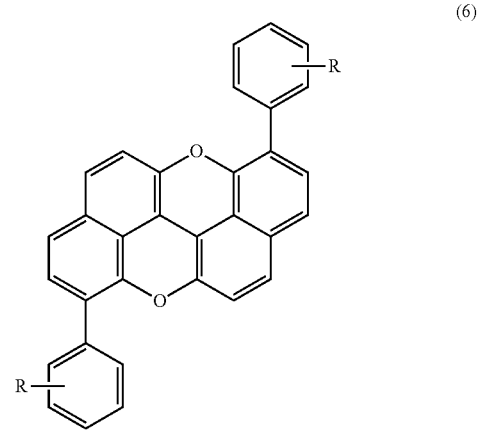

(where R is an alkyl group)

(7)

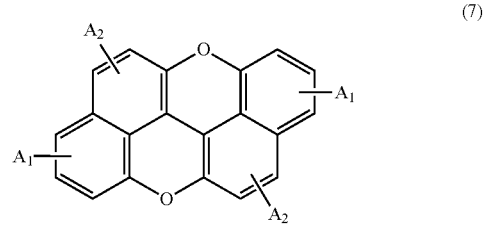

(where A1 and A2 are represented by Formula 8)

(8)

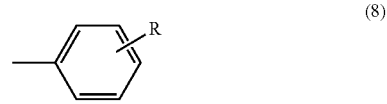

(where R is an alkyl group or another substituent).

12 Claims, 4 Drawing Sheets

METHOD FOR PRODUCING ORGANIC TRANSISTOR, ORGANIC TRANSISTOR, METHOD FOR PRODUCING SEMICONDUCTOR DEVICE, SEMICONDUCTOR DEVICE, AND ELECTRONIC APPARATUS

TECHNICAL FIELD

The present disclosure relates to a method for producing an organic transistor, an organic transistor, a method for producing a semiconductor device, a semiconductor device, and an electronic apparatus. More specifically, the present disclosure relates to a method for producing an organic transistor using a dioxaanthanthrene-based compound, an organic transistor, a method for producing a semiconductor device, a semiconductor device, and an electronic apparatus using the organic transistor or the semiconductor device.

BACKGROUND ART

In the related art, as an active layer (a semiconductor film) in a semiconductor device such as a field effect transistor, an inorganic-based semiconductor material represented by silicon is used.

However, the semiconductor device using the semiconductor film formed of the inorganic-based semiconductor material such as silicon has disadvantages as follows. Firstly, since a vacuum process, a high-temperature heat treatment, or the like is necessary, a large amount of energy is consumed. Secondly, since a high-temperature heat treatment is necessary, a type of substrate to be used is limited. Thirdly, investment in an expensive facility for fabrication is necessary. Fourthly, since the inorganic-based semiconductor material is hard and brittle, durability for bending or tensile stress is low.

In recent years, a semiconductor device including a semiconductor film formed of an organic semiconductor material has received attention. The semiconductor device has advantages as follows, as compared with a semiconductor device using a semiconductor film formed of an inorganic-based semiconductor material. Firstly, the semiconductor film can be formed at a low temperature. Secondly, since the organic semiconductor material is soluble in a solvent, the semiconductor film can be formed by coating. Thirdly, since the organic semiconductor material is soluble in a solvent, the semiconductor film can be formed by a printing method. Fourthly, since the semiconductor film can be easily formed by a coating or printing method, it has advantageous in terms of an increase in an area of the semiconductor film. Fifthly, since the semiconductor film can be formed at a low temperature, the semiconductor film can be formed on a flexible substrate which has low heat resistance, but is flexible, which is formed of a plastic, or the like, and thus a flexible semiconductor device can be fabricated. Sixthly, since characteristics of the semiconductor film can be controlled through substituent control of the organic semiconductor material, multiple functions and high performance of a semiconductor device can be attempted. Seventhly, low costs of a semiconductor device can be attempted.

Until now, as the organic semiconductor material suitable for coating or printing, pentacene derivatives, poly(alkyl thiophene)s, and the like have been used, and development in fabrication of a field effect transistor by a wet process using the organic semiconductor materials has been conducted. However, carrier mobility of the field effect transistor is equal to or less than $0.1 \text{ cm}^2\text{V}^{-1}\text{s}^{-1}$, and is smaller than $1 \text{ cm}^2\text{V}^{-1}\text{s}^{-1}$, which is mobility of a field effect transistor (a thin film transistor) using amorphous silicon of the related art.

Further, as compared with an inorganic semiconductor material, the organic semiconductor material has a problem related to carrier injection. That is, in general, it is said that in organic molecules, a molecule having a shallow HOMO (highest occupied molecular orbital) is unstable. In fact, in polyacene compounds, it is said that since anthracene having a short ring length has a deeper HOMO than pentacene having a long ring length, anthracene is stable. However, in a stable organic molecule having a deep HOMO, when a general metal is used as an electrode material, since a large energy difference between an HOMO of the organic molecule and a work function of the metal is occurred, effective carrier injection is expected to be inhibited by a Schottky barrier.

Further, the organic semiconductor material is unstable in the atmosphere or at a high temperature, as compared with the inorganic semiconductor material. That is, as described above, an organic molecule, which is capable of satisfactory performing carrier injection on an electrode, has a shallow HOMO, but the organic molecule is likely to be unstable in the atmosphere or at a high temperature. Further, it is known that the organic semiconductor material is decomposed through a reaction of its own material to oxygen. Based these reasons, it is known that characteristics of the semiconductor device using the semiconductor film formed of the organic semiconductor material are deteriorated.

Further, in a semiconductor device using a semiconductor film formed by spin-coating a solution in which an organic semiconductor material is dissolved in a solvent, it is difficult to secure characteristic uniformity in the plane. This is regarded to be caused by coating unevenness when the solution containing the organic semiconductor material is spin-coated.

In recent years, to solve the problems of the semiconductor device using the semiconductor film formed of the organic semiconductor material, by the inventors, it is suggested using a dioxaanthanthrene-based compound, such as 6,12-dioxaanthanthrene (also known as peri xanthenoxanthene, 6,12-dioxaanthanthrene (may be abbreviated as "PXX")) as the organic semiconductor material (see Non-Patent Literature 1 and Patent Literature 1). When the dioxaanthanthrene-based compound is used, the above-described problems caused in the case in which the semiconductor film formed of the organic semiconductor material is used can be solved. For example, PXX is stable in the atmosphere and has excellent heat resistance (see Non-Patent Literature 1).

CITATION LIST

Patent Literature
Patent Literature 1: JP 2010-006794A
Non-Patent Literature
Non-Patent Literature 1: N. Kobayashi, M. Sasaki and K. Nomoto: Chem. Mater. 21 (2009) 552

SUMMARY OF INVENTION

Technical Problem

However, when the organic semiconductor film is formed using the above-described dioxaanthanthrene-based compound, since the organic semiconductor film is formed on a gate insulating film after the gate insulating film is formed, or a gate insulating film is formed on the organic semiconductor film after the organic semiconductor film using the dioxaanthanthrene-based compound is formed, it is difficult to form a satisfactory interface between the organic semiconductor film and the gate insulating film. Therefore, it is difficult to obtain sufficiently high carrier mobility in the organic transistor.

Therefore, it is desirable to provide an organic transistor and a method for producing the same capable of obtaining sufficiently high carrier mobility.

Further, it is desirable to provide a semiconductor device, such as an organic transistor, and a method for producing the same capable of obtaining sufficiently high carrier mobility.

Further, it is desirable to provide an electronic apparatus using the excellent organic transistor or semiconductor device.

The object and the other objects may be apparent from the following description of the specification.

Solution to Problem

According to an embodiment of the present disclosure, there is provided a method of producing an organic transistor, the method including collectively forming a gate insulating film and an organic semiconductor film by applying, onto a gate electrode disposed on a base substrate, a solution including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the gate insulating film containing the polymer, the organic semiconductor film being formed on the gate insulating film and containing the at least one compound, and forming a source electrode and a drain electrode on the organic semiconductor film.

[Chem. 1]

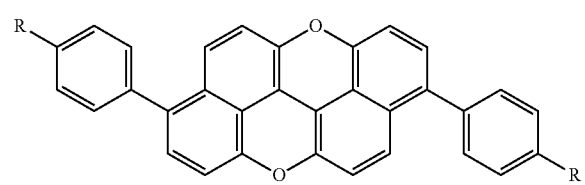

(1)

(where R is a linear or branched alkyl group)

[Chem. 2]

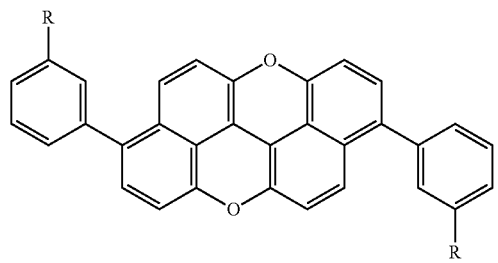

(2)

(where R is a linear or branched alkyl group)

[Chem. 3]

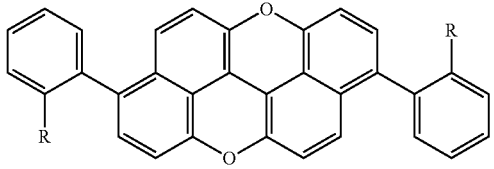

(3)

(where R is a linear or branched alkyl group)

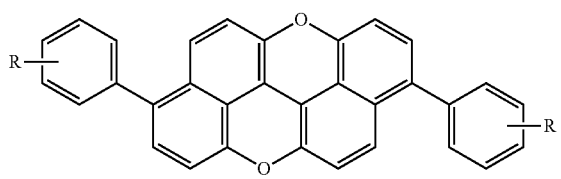

(4)

(where R is an alkyl group, and a number of R's is 2 to 5)

[Chem. 5]

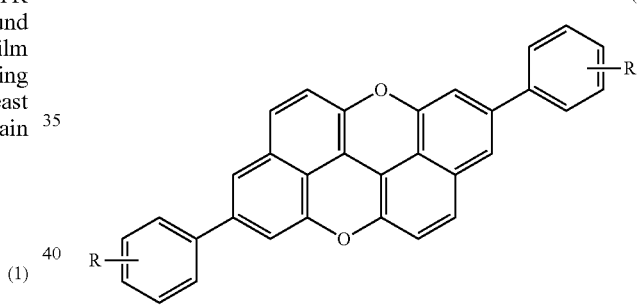

(5)

(where R is an alkyl group, and a number of R's is 1 to 5)

[Chem. 6]

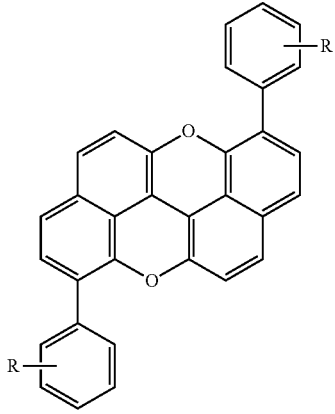

(6)

(where R is an alkyl group, and a number of R's is 1 to 5)

[Chem. 7]

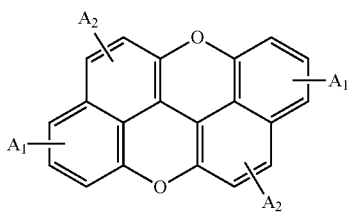

(7)

(where A1 and A2 are represented by Formula 8)

[Chem. 8]

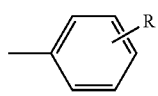

(8)

(where R is an alkyl group or another substituent, and a number of R's is 1 to 5)

Further, according to an embodiment of the present disclosure, there is provided an organic transistor including a gate insulating film and an organic semiconductor film collectively formed by applying, onto a gate electrode disposed on a base substrate, a solution including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the gate insulating film containing the polymer, the organic semiconductor film being formed on the gate insulating film and containing the at least one compound, and a source electrode and a drain electrode disposed on the organic semiconductor film.

Further, according to an embodiment of the present disclosure, there is provided an electronic apparatus including an organic transistor which includes a gate insulating film and an organic semiconductor film collectively formed by applying, onto a gate electrode disposed on a base substrate, a solution including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the gate insulating film containing the polymer, the organic semiconductor film being formed on the gate insulating film and containing the at least one compound, and a source electrode and a drain electrode disposed on the organic semiconductor film.

Further, according to an embodiment of the present disclosure, there is provided a method of producing a semiconductor device, the method including collectively forming an insulating film and an organic semiconductor film by applying, onto a base substrate, a solution including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the insulating film containing the polymer, and the organic semiconductor film formed on the insulating film and containing the at least one compound.

Further, according to an embodiment of the present disclosure, there is provided a semiconductor device including an insulating film and an organic semiconductor film collectively formed by applying, onto a base substrate, a solution including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the insulating film containing the polymer, the organic semiconductor film being formed on the insulating film and containing the at least one compound.

Further, according to an embodiment of the present disclosure, there is provided an electronic apparatus including a semiconductor device which includes an insulating film and an organic semiconductor film collectively formed by applying, onto a base substrate, a solution including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the insulating film containing the polymer, the organic semiconductor film formed on the insulating film and containing the at least one compound.

It is preferable, but not limited to, that the at least one compound is one compound represented by the following Formulas 9 to 17.

[Chem. 9]
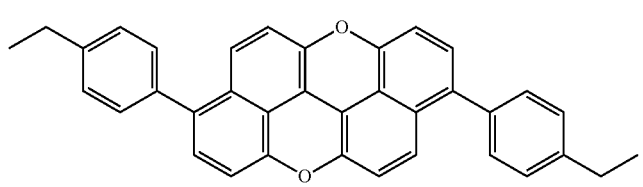
(9)
[Chem. 10]
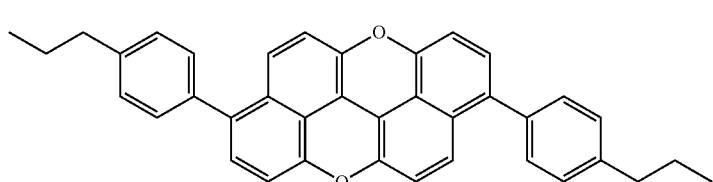
(10)
[Chem. 11]
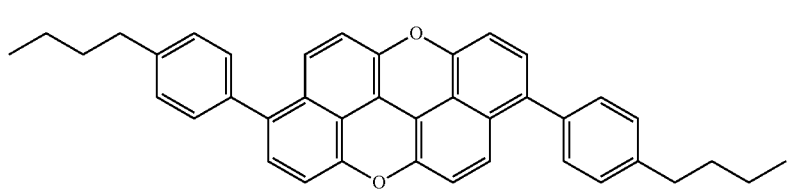
(11)
[Chem. 12]
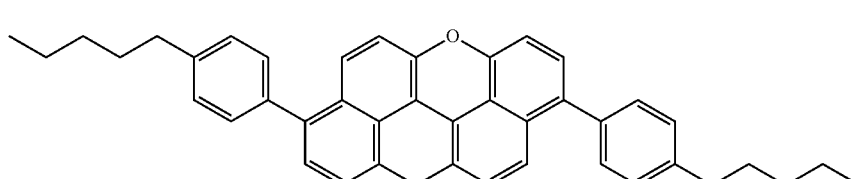
(12)
[Chem. 13]
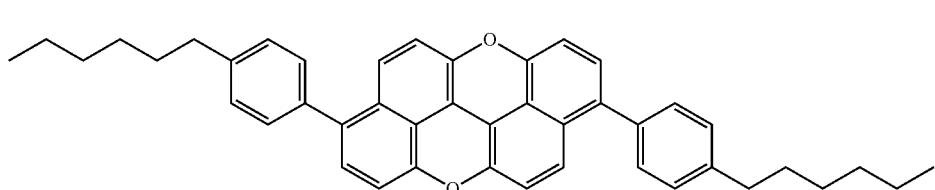
(13)
[Chem. 14]
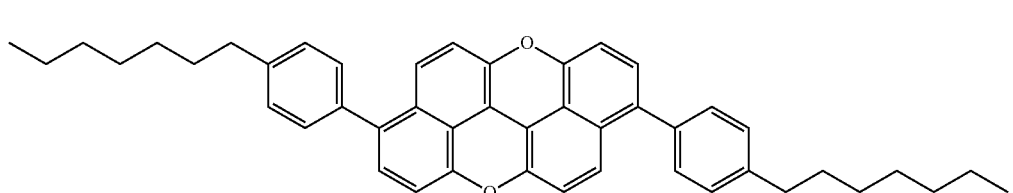
(14)
[Chem. 15]
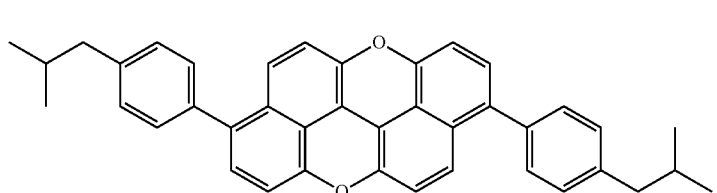
(15)

[Chem. 16]

(16)

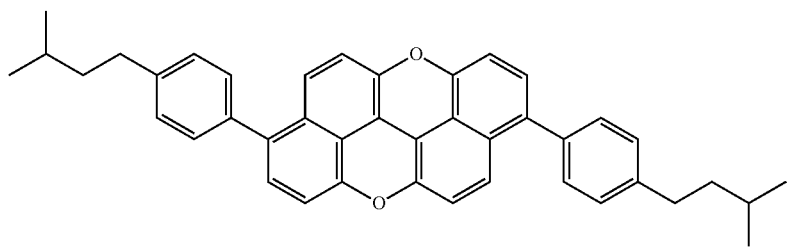

[Chem. 17]

(17)

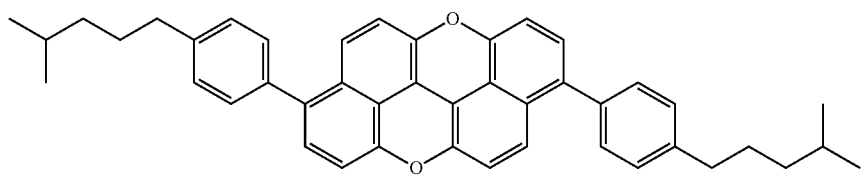

When applying, onto a gate electrode disposed on a base substrate or the base substrate, a solution including a polymer and an organic semiconductor film including at least one compound among a compound represented by General Formula 1, a compound represented by General Formula 2, a compound represented by General formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, spontaneous phase-separation is in a process of drying the solution, and a gate insulating film or insulating film containing the polymer, and an organic semiconductor film continuously formed with the gate insulating film or insulating film on the gate insulating film or insulating film and containing the at least one compound are obtained. The gate insulating film and the organic semiconductor film may be formed by forming an organic insulating film containing a portion of the gate insulating film on the gate electrode and applying the solution onto the organic insulating film.

In the organic transistor and the semiconductor device, as the polymer, an insulating polymer capable of forming an insulating film may be used, preferably, at least one of poly(α-methylstyrene) and a cycloolefin copolymer may be used, but the polymer is not limited thereto.

As a solvent of the solution, conventionally known solvents may be used, and the solvent is selected as needed. However, a specific example of the solvent is at least one among xylene, p-xylene, mesitylene, toluene, tetralin, anisole, benzene, 1,2-dichlorobenzene, o-dichlorobenzene, cyclohexane, and ethyl cyclohexane. A dry condition (temperature, time, and the like) of the solution is appropriately selected according to the used solvent.

As long as the semiconductor device has a structure in which an organic semiconductor film and an insulating film are disposed to be in contact with each other, the semiconductor device may have basically all structures. The semiconductor device includes the organic transistor having a structure in which an organic semiconductor film and a gate insulating film are disposed to be in contact with each other, but for example, the semiconductor device may include a capacitor having a structure in which an insulating film is interposed between an organic semiconductor film and another conductive film (for example, an organic semiconductor film, a metal film, or the like).

The electronic apparatus may be a variety of electronic apparatuses using an organic transistor or a semiconductor device, and may include both a portable electronic apparatus and a stationary electronic apparatus, and a function or use thereof is not used. For example, specific examples of the electronic apparatus may include a display such as a liquid crystal display or an organic electroluminescence display, a portable phone, a mobile apparatus, a personal computer, a game machine, car equipment, a household electrical appliance, an industrial product, and the like.

In the present disclosure described above, as a gate insulating film and insulating film containing the polymer, and an organic semiconductor film continuously formed with the gate insulating film or insulating film on the gate insulating film or insulating film and containing the at least one compound are obtained by applying a solution including a polymer and at least one compound among a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, a satisfactory interface between an organic semiconductor film and a gate insulating film or a satisfactory interface between the organic semiconductor film and an insulating film can be simply obtained.

Advantageous Effects of Invention

According to the present disclosure, as a satisfactory interface between an organic semiconductor film and a gate insulating film can be obtained, an organic transistor in which carrier scattering in the interface between the organic semiconductor film and the gate insulating film does not occur and which has sufficiently high carrier mobility can be obtained. Further, as the satisfactory interface between the organic semiconductor film and the gate insulating film can be obtained, a semiconductor device such as an organic transistor having sufficiently high carrier mobility or a capacitor having satisfactory characteristics can be obtained. In addition, various advantages can be obtained by using an organic semiconductor film including at least one compound among a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7. In addition, a high-performance electronic apparatus can be realized by using the excellent organic transistor or semiconductor device.

DESCRIPTION OF EMBODIMENTS

Hereinafter, modes for carrying out the present invention (hereinafter referred to as "embodiments") will be described. The description will be made in the following order.

1. First embodiment (organic transistor and method for producing the same)
2. Second embodiment (capacitor and method for producing the same)

1. First Embodiment

Organic Transistor

Figure 1:
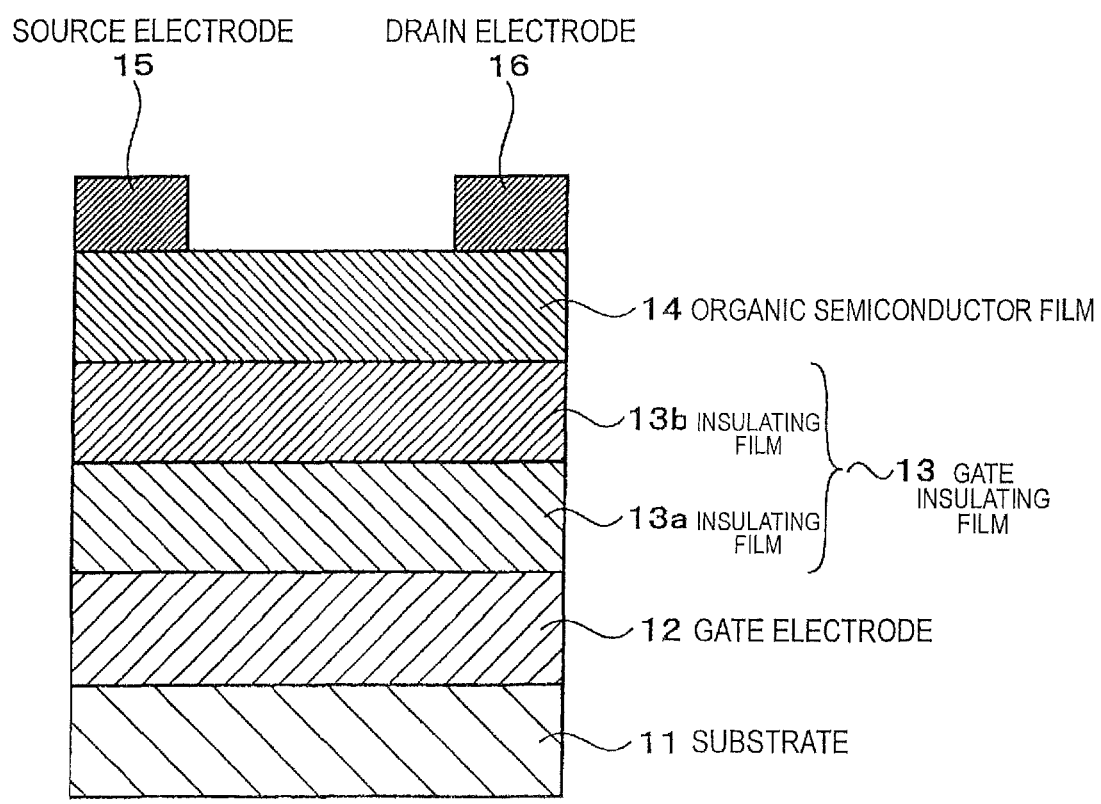
FIG. 1 is a cross-sectional view illustrating an organic transistor according to a first embodiment.

FIG. 1 illustrates an organic transistor according to a first embodiment.

As illustrated in FIG. 1, in an organic transistor, a gate electrode 12 is disposed on a substrate 11. A gate insulating film 13 is disposed to cover the gate electrode 12. The gate insulating film 13 has a double-layered structure of an insulating film 13a and an insulating film 13b formed thereon. An organic semiconductor film 14 which is a channel region is disposed on the gate insulating film 13. A source electrode 15 and a drain electrode 16 are disposed on the organic semiconductor film 14. A top-contact bottom-gate organic transistor having a configuration of an insulated gate field effect transistor is constituted by the gate electrode 12, the organic film 14, the source electrode 15, and the drain electrode 16.

The organic semiconductor film 14 includes at least one compound among a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, preferably, a compound of any one represented by Formulas 9 to 17. A lower-layered insulating film 13a of the gate insulating film 13 includes, for example, an organic insulator such as PVP-RSiCl$_3$, DAP, or isoDAP. Further, an upper-layered insulating film 13b of the gate insulating film 13 is selected, for example, from among previously mentioned polymers as necessary. As the polymer, preferably, at least one of poly($\alpha$-methylstyrene) and a cycloolefin copolymer may be used. As the cycloolefin copolymer, TOPAS (registered trademark) (manufactured by TOPAS ADVANCED POLYMERS GmbH) represented by the following structural formula may be used.

[Chem. 18]

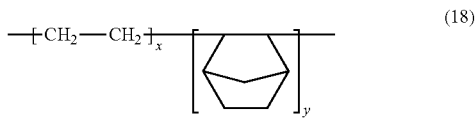

(18)

In this case, the organic semiconductor film 14 and the upper-layered insulating film 13b of the gate insulating film 13 are continuously formed in a thickness direction thereof. Thicknesses of the gate insulating film 13 and the organic semiconductor film 14 are appropriately selected according to characteristics necessary for the organic transistor.

A material of the substrate 11 is selected from among conventionally known materials as necessary, and may be a transparent material or a material opaque to visible light. Further, the substrate 11 may be conductive or non-conductive. The substrate 11 may be flexible or non-flexible. Specifically, examples of the material of the substrate 11 may include a variety of plastics (organic polymers) such as polymethyl methacrylate (PMMA), polyvinyl alcohol (PVA), polyvinyl phenol (PVP), polyether sulfone (PES), polyimide, polycarbonate, polyethylene terephthalate (PET), or polyethylene naphthalate (PEN), mica, a variety of glass substrates, a quartz substrate, a silicon substrate, a variety of alloys such as stainless steel, and a variety of metals. By using plastic as the material of the substrate 11, the substrate 11 may be made to be flexible, and thus, a flexible organic transistor may be obtained.

Examples of a material containing the gate electrode 12, the source electrode 15, and the drain electrode 16 may include a metal such as platinum (Pt), gold (Au), palladium (Pd), chromium (Cr), molybdenum (Mo), nickel (Ni), aluminum (Al), silver (Ag), tantalum (Ta), tungsten (W), copper (Cu), titanium (Ti), indium (In), or tin (Sn), or a variety of conductive materials such as alloys containing the metal elements, conductive particles formed of the metals, conductive particles formed of the alloys containing the metals, and polysilicon containing impurities. Examples of the material containing the gate electrode 12, the source electrode 15, and the drain electrode 16 may include organic materials (conductive polymers) such as poly(3,4-ethylenedioxythiophene)/polystyrene sulfonic acid (PEDOT/PSS). The gate electrode 12, the source electrode 15, and the drain electrode 16 may have a laminated structure of two or more kinds of layers made of the. A width (a gate length) of the gate electrode 12 in a length direction of a channel or a distance (a channel length) between the source electrode 15 and the drain electrode 16 is appropriately selected according to characteristics and the like necessary for the organic transistor.

[Method for Producing Organic Transistor]

Figure 2A:
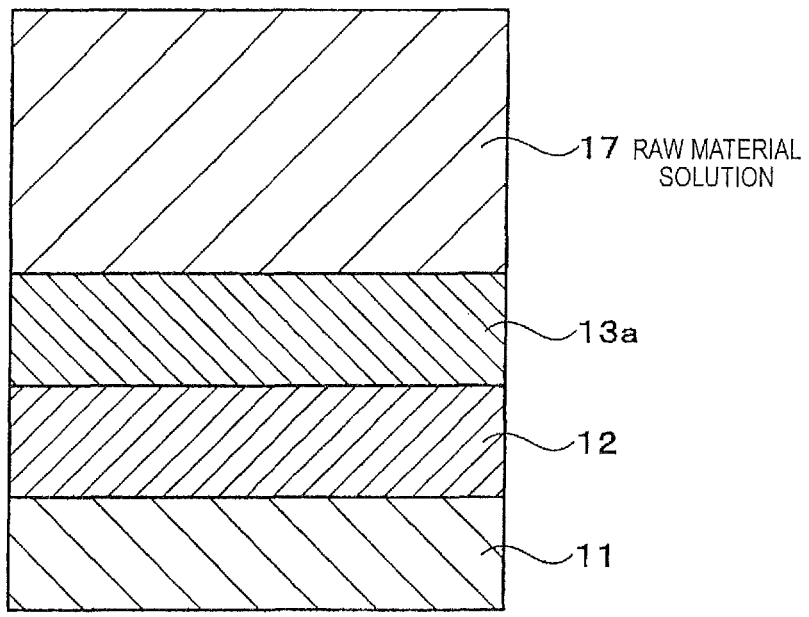
FIG. 2A is a cross-sectional view illustrating a method for producing the organic transistor according to the first embodiment.
Figure 2B:
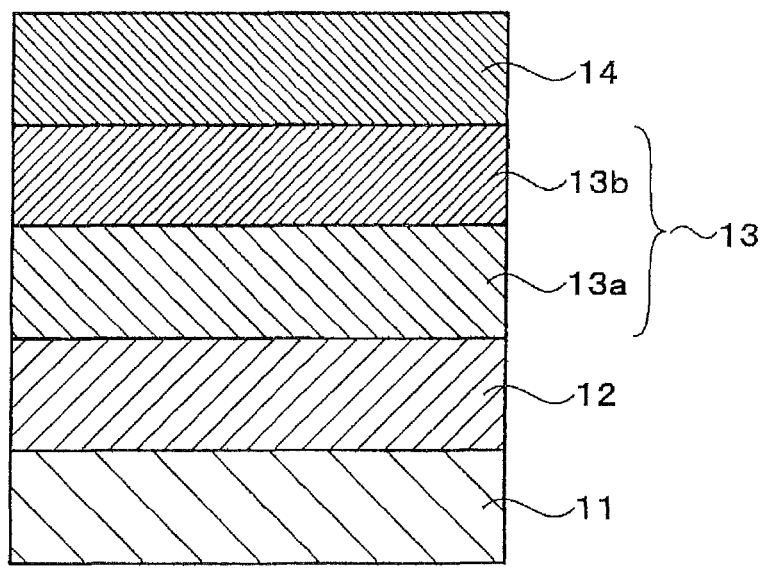
FIG. 2B is a cross-sectional view illustrating a method for producing the organic transistor according to the first embodiment.

FIGS. 2A and 2B illustrate a method for producing the organic transistor.

As illustrated in FIG. 2A, first, by a conventionally known method, a gate electrode 12 is formed on a substrate 11, and an insulating film 13a is thereon.

On the other hand, a raw material solution containing at least one compound among a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, preferably, a compound of any one represented by Formulas 9 to 17, and the previously mentioned insulating polymer is prepared. A solvent of the raw material solution is appropriately selected from among the previously mentioned solvents. Further, a mixing ratio (a mass ratio or a weight ratio) of the compound and the insulating polymer in the raw material solution is selected as necessary.

Next, as illustrated in FIG. 2B, the raw material solution 17 prepared in this way is coated or printed on the insulating film 13a in a film shape. Examples of the coating method of the raw material solution 17 may include a spin coat method and the like. Examples of the printing method of a raw material solution 18 may include a screen printing method, an inkjet printing method, an offset printing method, a reverse offset printing method, a gravure printing method, a microcontact method, and the like. Examples of a coating or printing method of the raw material solution 17 may include a variety of coating methods such as an air doctor coater method, a blade coater method, a rod coater method, a knife coater method, a squeeze coater method, a reverse roll coater method, a transfer roll coater method, a gravure coater method, a kiss coater method, a cast coater method, a spray coater method, a slit orifice coater method, a calendar coater method, and a dipping method.

Next, the film-shaped raw material solution 17 is dried. In a process of the drying, the at least one compound among the compound represented by General Formula 1, the compound represented by General Formula 2, the compound represented by General Formula 3, the compound represented by General Formula 4, the compound having a structure represented by General Formula 4, wherein R is a substituent other than an alkyl group, a compound represented by General Formula 5, the compound represented by General Formula 6, the compound having a structure represented by General Formula 5 or 6, wherein R is a substituent other than an alkyl group, and the compound represented by General Formula 7, and the insulating polymer contained in the raw material solution 17 are spontaneously phase-separated into layer shapes. As a result, after the drying, as illustrated in FIG. 2B, an insulating film 13b formed of the insulating polymer and an organic semiconductor film 14 formed thereon and formed of the compound are continuously formed in a thickness direction.

Next, as necessary, the organic semiconductor film 14 formed in this way is patterned in a predetermined shape by etching or the like, and then a source electrode 16 and a drain electrode 17 are formed on the organic semiconductor film 14 by a conventionally known method.

Therefore, the desired top-contact bottom-gate organic transistor is produced.

Example 1

A raw material solution was prepared by uniformly dissolving a compound (abbreviated as C2Ph-PXX) represented by Formula 9 and poly(α-methylstyrene) (abbreviated as p-αMS), which is an insulating polymer, in mesitylene.

The raw material solution prepared in this way was coated on a substrate in which a gate electrode is formed by a spin coat method. As the substrate, a glass substrate of which a surface is covered with an organic insulating film containing cross-linked polyvinyl phenol (PVP) as a main component was used.

Figure 3:
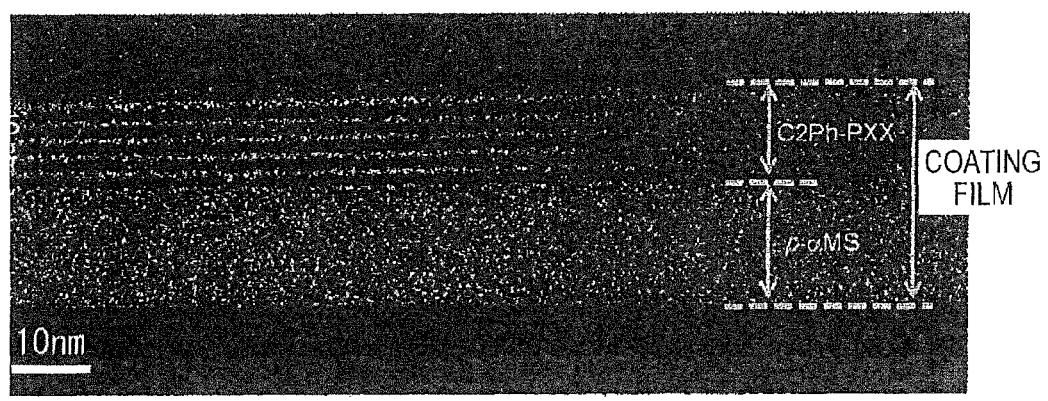
FIG. 3 is a figure-substitute photograph illustrating a cross-sectional transmission electron microscope photograph of an example of a laminated structure of an organic semiconductor film and the insulating polymer film formed by phase-separation from a raw material solution.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of C2Ph-PXX formed thereon was formed. FIG. 3 illustrates a cross-sectional transmission electron microscope photograph of a sample. As can be seen from FIG. 3, the gate insulating film formed of poly(α-methylstyrene) and having a thickness of about 15 nm and the organic semiconductor film formed of C2Ph-PXX and having a thickness of about 10 nm formed thereon form a distinct interface and are continuously formed.

Thereafter, a source electrode and a drain formed of gold (Au) were formed on the organic semiconductor film formed of C2Ph-PXX with a chromium (Cr) film interposed as an adhesion layer therebetween. In this way, a bottom gate organic transistor was produced.

Example 2

A raw material solution was prepared by uniformly dissolving a compound (abbreviated as C3Ph-PXX) represented by Formula 10 and poly(α-methylstyrene) (p-αMS), which is an insulating polymer, in mesitylene.

The raw material solution prepared in this way was coated on a substrate by a spin coat method. The same substrate as in Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of C3Ph-PXX formed thereon was formed.

Thereafter, in the same manner as in Example 1, a bottom gate organic transistor was produced.

Example 3

A raw material solution was prepared by uniformly dissolving a compound (abbreviated as C4Ph-PXX) represented by Formula 11 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of C4Ph-PXX formed thereon was formed.

Thereafter, in the same manner as in Example 1, a bottom gate organic transistor was produced.

Example 4

A raw material solution was prepared by uniformly dissolving a compound (abbreviated as C5Ph-PXX) represented by Formula 12 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of C5Ph-PXX formed thereon was formed.

Thereafter, in the same manner as in Example 1, a bottom gate organic transistor was produced.

Example 5

A raw material solution was prepared by uniformly dissolving a compound (abbreviated as C6Ph-PXX) represented by Formula 13 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of C6Ph-PXX formed thereon was formed.

Thereafter, in the same manner as in Example 1, a bottom gate organic transistor was produced.

Example 6

A raw material solution was prepared by uniformly dissolving a compound (abbreviated as C9Ph-PXX) represented by Formula 14 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of C9Ph-PXX formed thereon was formed.

Example 7

A raw material solution was prepared by uniformly dissolving a compound (abbreviated as iC4Ph-PXX) represented by Formula 15 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of iC4Ph-PXX formed thereon was formed.

Example 8

A raw material solution was prepared by uniformly dissolving a compound (abbreviated as iC5Ph-PXX) represented by Formula 16 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of iC5Ph-PXX formed thereon was formed.

Example 9

A raw material solution was prepared by uniformly dissolving a compound (abbreviated as iC6Ph-PXX) represented by Formula 17 and poly(α-methylstyrene) (p-αMS), which is an insulating polymer, in mesitylene.

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of iC6Ph-PXX formed thereon was formed.

Comparative Example 1

A raw material solution was prepared by uniformly dissolving a compound represented by the following Formula 19 and poly(α-methylstyrene) (p-αMS), which is an insulating polymer, in mesitylene.

[Chem. 19]

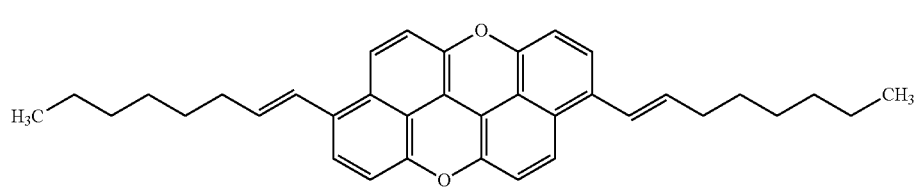

(19)

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of the compound represented by Formula 19 formed thereon was formed.

Comparative Example 2

A raw material solution was prepared by uniformly dissolving a compound represented by the following Formula 20 and poly(α-methylstyrene) (p-αMS), which is an insulating polymer, in mesitylene.

[Chem. 20]

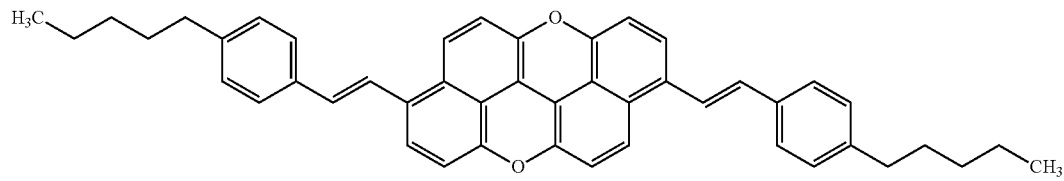

(20)

The raw material solution prepared in this way was coated on a substrate by a spin coat method. The same substrate as Example 1 was used as the substrate.

Next, the coating film formed in this way was dried in a nitrogen atmosphere at 60° C. for 1 hour. Accordingly, spontaneous phase-separation was caused in the coating film, and a laminated structure of a gate insulating film formed of poly(α-methylstyrene) and an organic semiconductor film formed of the compound represented by Formula 20 formed thereon was formed.

Carrier mobility of the organic transistors of Examples 1 to 9 and Comparative Examples 1 and 2 was measured. Measurement results of the carrier mobility of the organic transistors of Examples 1 to 9 are shown in Table 1. On the other hand, organic transistors were produced by forming organic semiconductor films by vacuum depositing C2Ph-PXX, C3Ph-PXX, and 9Ph-PXX. Here, before the organic semiconductor films were formed, gate insulating films formed of poly(α-methylstyrene) were formed in advance. In Table 1, the measurement results of the carrier mobility of the organic transistors are also shown. In Comparative Examples 1 and 2, organic transistors were also produced by forming organic semiconductor films by vacuum depositing the compound represented by Formula 19 or 20. Here, before the organic semiconductor films were formed, gate insulating films formed of poly(α-methylstyrene) were formed in advance. The measurement of the carrier mobility of the organic transistors was performed.

TABLE 1

|  | Mobility (polymer mixture) cm$^2$/Vs | Mobility (deposition) cm$^2$/Vs |
| --- | --- | --- |
| Example 1 (C2Ph-PXX) | 0.9 | 0.48-0.65 |
| Example 2 (C3Ph-PXX) | 1.1 | 0.60-0.81 |
| Example 3 (C4Ph-PXX) | 0.68 |  |
| Example 4 (C5Ph-PXX) | 0.60 |  |
| Example 5 (C6Ph-PXX) | 1.3 |  |
| Example 6 (C9Ph-PXX) | 1.3 | 0.41-0.65 |

TABLE 1-continued

|  | Mobility (polymer mixture) cm$^2$/Vs | Mobility (deposition) cm$^2$/Vs |
| --- | --- | --- |
| Example 7 (iC4Ph-PXX) | 0.80 |  |
| Example 8 (iC5Ph-PXX) | 1.0 |  |
| Example 9 (iC6Ph-PXX) | 0.74 |  |

As shown in Table 1, in all the organic transistors of Examples 1 to 9, the carrier mobility was greatly improved overall as compared with the organic transistors using the organic semiconductor films formed by vacuum depositing C2Ph-PXX, C3Ph-PXX, and C9Ph-PXX. The carrier mobility is comparable to carrier mobility of a field effect transistor using amorphous silicon. The great improvement of the carrier mobility is due to a good interface between the gate insulating film and the organic semiconductor film formed by coating a uniform raw material solution containing C2Ph-PXX, C3Ph-PXX, C4Ph-PXX, C5Ph-PXX, C6Ph-PXX, C9Ph-PXX, iC4Ph-PXX, iC5Ph-PXX, or iC6Ph-PXX and poly(α-methylstyrene), which is a polymer, and allowing spontaneous phase-separation to be expressed in a drying process of the coating film.

Measurement of carrier mobility of the organic transistors of Comparative Examples 1 and 2 and the organic transistor using the organic semiconductor film formed by vacuum depositing the compound represented by Formula 19 or 20 was performed. An improvement effect in the carrier mobility cannot be obtained by forming the organic semiconductor film using the raw material solution to which poly(α-methylstyrene) was added as the polymer in addition to the compound represented by Formula 19 or 20.

As described above, according to the first embodiment, by obtaining the good interface between the organic semiconductor film 15 and the gate insulating film 14, a high-performance organic transistor having sufficiently high carrier mobility as compared with the organic transistor in the related art can be realized. Further, in the organic semiconductor film 14 formed of at least one compound among a compound represented by General Formula 1, a compound represented by General Formula 2, a compound represented by General Formula 3, a compound represented by General Formula 4, a compound having a structure represented by General Formula 4, wherein R is a substituent other than an alkyl group, a compound represented by General Formula 5, a compound represented by General Formula 6, a compound having a structure represented by General Formula 5 or 6, wherein R is a substituent other than an alkyl group, and a compound represented by General Formula 7, since resistance to oxygen in the atmosphere, light resistance, heat resistance, water resistance, and solvent-resistance are highly stable, an organic transistor having high stability can be realized. Further, since the organic semiconductor film 14 has high process resistance, a degree of freedom in design of a production process of the organic transistor is high, and a width of the process can be widened.

2. Second Embodiment

Capacitor

Figure 4:
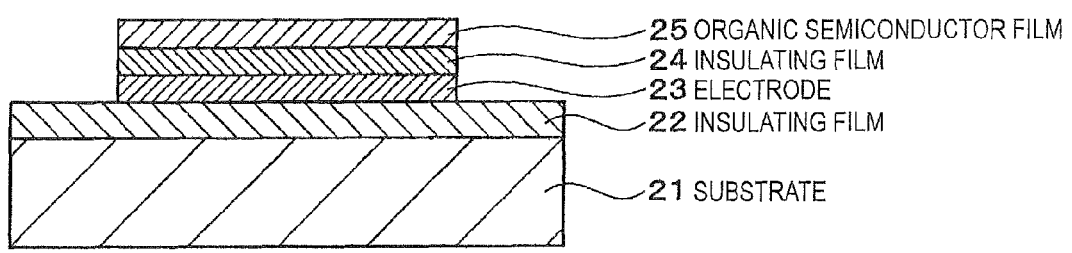
FIG. 4 is a cross-sectional view illustrating a capacitor according to a second embodiment.

FIG. 4 illustrates a capacitor according to a second embodiment.

As illustrated in FIG. 4, in the capacitor, an insulating film 22 is disposed on a substrate 21. An electrode 23, an insulating film 24 as a dielectric, and an organic semiconductor film 25 are sequentially laminated on the insulating film 22, and therefore the capacitor is formed. The electrode 23 constitutes a lower electrode of the capacitor, and the organic semiconductor film 25 constitutes an upper electrode of the capacitor.

Like the organic semiconductor film 14 according to the first embodiment, the organic semiconductor film 25 is formed of at least one compound among a compound represented by General Formula 1, a compound represented by General Formula 2, a compound represented by General Formula 3, a compound represented by General Formula 4, a compound having a structure represented by General Formula 4, wherein R is a substituent other than an alkyl group, a compound represented by General Formula 5, a compound represented by General Formula 6, a compound having a structure represented by General Formula 5 or 6, wherein R is a substituent other than an alkyl group, and a compound represented by General Formula 7. Further, like the insulating film 13b of the gate insulating film 13 according to the first embodiment, the insulating film 24 includes an insulating polymer capable of forming an insulating film, and the polymer is selected from among the previously mentioned polymers as needed. At this time, the organic semiconductor film 25 and the insulating film 24 are continuously formed in a thickness direction thereof by mutual phase-separation. A thickness of the insulating film 24 is appropriately selected according to characteristics and the like required for the capacitor. As the electrode 23, an organic semiconductor film, a metal film, an alloy film, and the like may be used.

As a material of the substrate 21, the same material as the substrate 11 of the first embodiment may be used. As a material of the insulating film 22, the same material as the insulating film 12 of the first embodiment may be used.

[Method for Producing Capacitor]

Figure 5A:
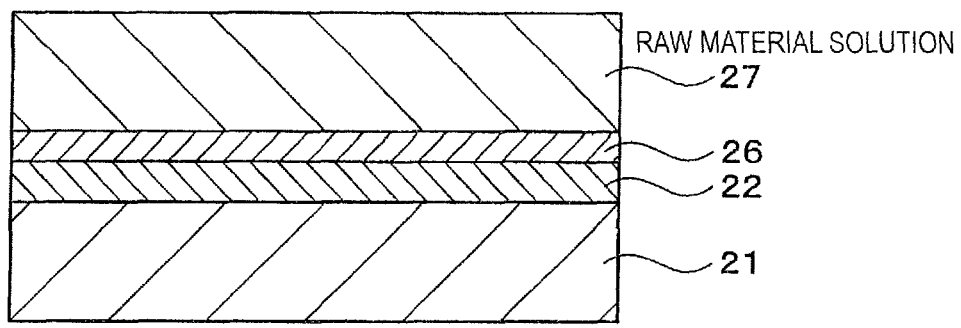
FIG. 5A is a cross-sectional view illustrating a method producing the capacitor according to the second embodiment.
Figure 5B:
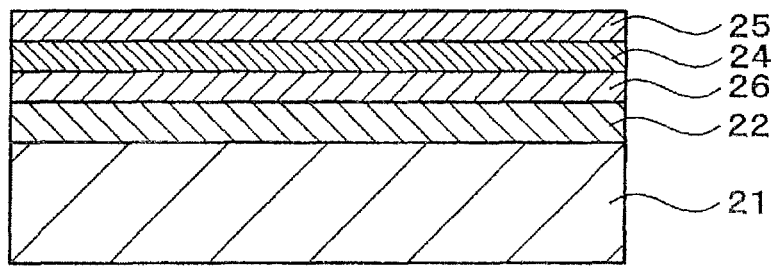
FIG. 5B is a cross-sectional view illustrating a method for producing the capacitor according to the second embodiment.

FIGS. 5A and 5B illustrate a method of producing the capacitor.

As illustrated in FIG. 5A, first, by a conventionally known method, an insulating film 22 is formed on an entire surface of a substrate 21, and a conductive film 26 is formed on the insulating film 22.

On the other hand, a raw material solution containing at least one compound among a compound represented by General Formula 1, a compound represented by General Formula 2, a compound represented by General Formula 3, a compound represented by General Formula 4, a compound having a structure represented by General Formula 4, wherein R is a substituent other than an alkyl group, a compound represented by General Formula 5, a compound represented by General Formula 6, a compound having a structure represented by General Formula 5 or 6, wherein R is a substituent other than an alkyl group, and a compound represented by General Formula 7, and the previously mentioned insulating polymer is prepared. A solvent of the raw material solution is appropriately selected from among the previously mentioned solvents. Further, a mixing ratio (a mass ratio or a weight ratio) of the compound and the insulating polymer in the raw material solution is selected as needed.

Next, as illustrated in FIG. 5B, the prepared raw material solution 27 is coated or printed on the substrate 21, in which the conductive film 26 is formed, in a film shape. As the coating or printing method of the raw material solution 27, the same method as in the first embodiment may be used.

Next, the film-shaped raw material solution 27 is dried. In the drying process, the compound and insulating polymer contained in the raw material solution 27 are spontaneously phase-separated into layer shapes. As a result, after the drying, as illustrated in FIG. 5B, an insulating film 24 formed of the insulating polymer and an organic semiconductor film 25 formed of the compound on the insulating film 24 are continuously formed in a thickness direction.

Next, the formed organic semiconductor film 25, the insulating film 24, and the conductive film 26 are patterned in a predetermined shape by etching or the like. An electrode 23 is formed by the patterned conductive film 26.

Therefore, the desired capacitor is produced.

According to the second embodiment, by obtaining a good interface between the organic semiconductor film 25 and the insulating film 24, the capacitor having a good charge retention characteristic can be realized. Further, in the organic semiconductor film 25 including at least one compound among a compound represented by General Formula 1, a compound represented by General Formula 2, a compound represented by General Formula 3, a compound represented by General Formula 4, a compound having a structure represented by General Formula 4, wherein R is a substituent other than an alkyl group, a compound represented by General Formula 5, a compound represented by General Formula 6, a compound having a structure represented by General Formula 5 or 6, wherein R is a substituent other than an alkyl group, and a compound represented by General Formula 7, since resistance to oxygen in the atmosphere, light resistance, heat resistance, water resistance, and solvent resistance are highly stable, the capacitor having high stability can be realized.

The embodiments and examples have been specifically described, but the technology is not limited to the embodiments and examples, and various modifications are possible.

For example, numerical values, structures, configurations, shapes, materials, and the like mentioned in the mode for carrying out and the embodiment are merely examples, and different numerical values, structures, configurations, shapes, materials, and the like may be used as needed.

REFERENCE SIGNS LIST 11 substrate
12 gate electrode
13 gate insulating film
13a insulating film
13b insulating film
14 organic semiconductor film
15 source electrode
16 drain electrode
17 raw material solution
21 substrate
22 insulating film
23 electrode
24 insulating film
25 organic semiconductor film
26 conductive film
27 raw material solution

The invention claimed is:

1. A method of producing an organic transistor, the method comprising:
   collectively forming a gate insulating film and an organic semiconductor film by applying, onto a gate electrode disposed on a base substrate, a raw material solution, in a film shape, including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, forming the gate insulating film and the organic semiconductor film on the gate insulating film by spontaneous phase separation; and forming a source electrode and a drain electrode on the organic semiconductor film

[Chem. 1]

(1)

(where R is a linear or branched alkyl group)

[Chem. 2]

(2)

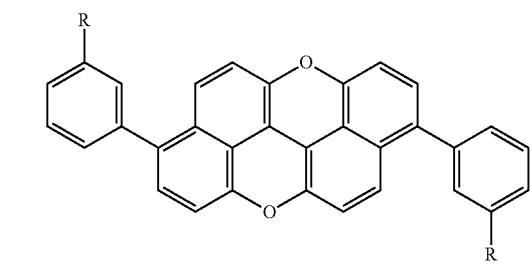

(where R is a linear or branched alkyl group)

[Chem. 3]

(3)

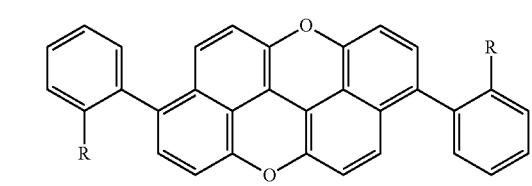

(where R is a linear or branched alkyl group)

[Chem. 4]

(4)

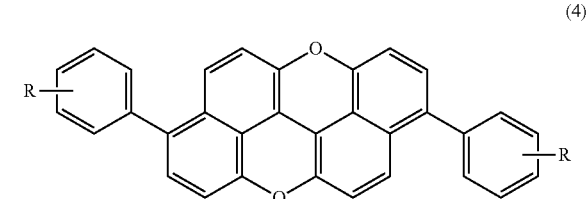

(where R is an alkyl group, and a number of R's is 2 to 5)

[Chem. 5]

(5)

(where R is an alkyl group, and a number of R's is 1 to 5)

[Chem. 6]

(6)

(where R is an alkyl group, and a number of R's is 1 to 5)

[Chem. 7]

(7)

(where A1 and A2 are represented by Formula 8)

[Chem. 8]

(8)

(where R is an alkyl group or another substituent, and a number of R's is 1 to 5).

2. The method according to claim 1, wherein the at least one compound is one compound represented by the following Formulas 9 to 17

[Chem. 9]
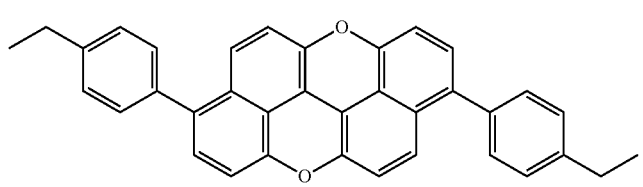
(9)
[Chem. 10]
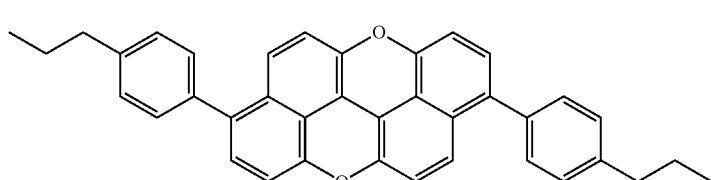
(10)
[Chem. 11]
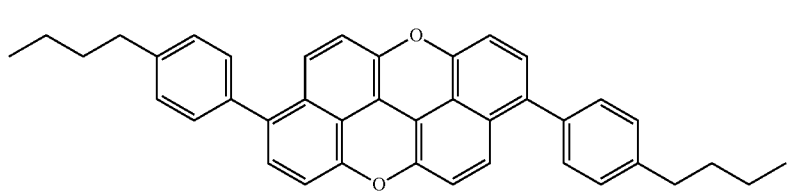
(11)
[Chem. 12]
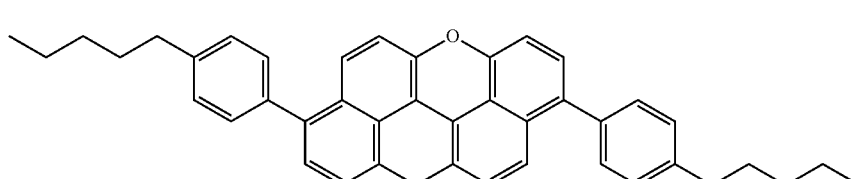
(12)
[Chem. 13]
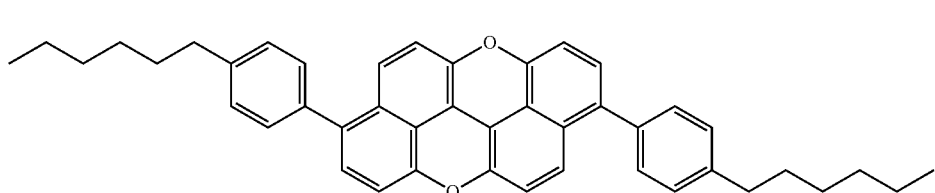
(13)
[Chem. 14]
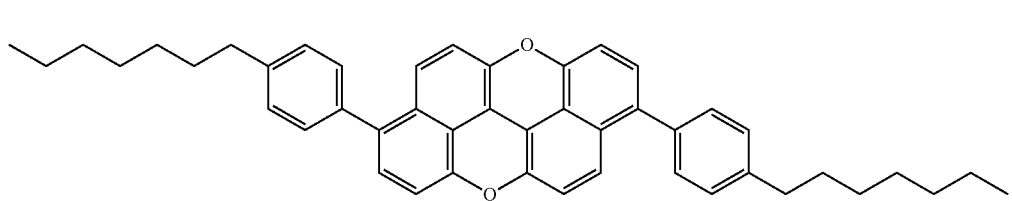
(14)
[Chem. 15]
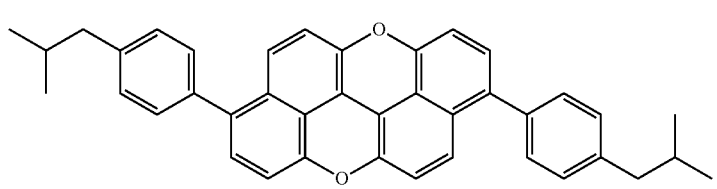
(15)

[Chem. 16]

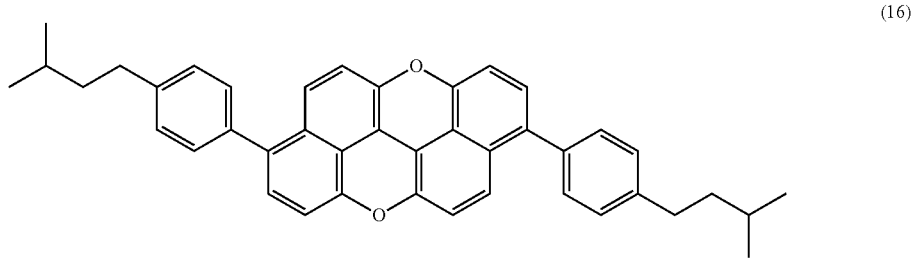

(16)

[Chem. 17]

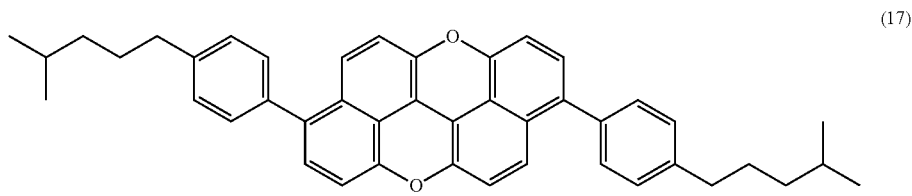

(17)

3. The method according to claim 1, wherein a solvent of the raw material solution is at least one of xylene, p-xylene, toluene, mesitylene, tetralin, anisole, benzene, 1,2-dichlorobenzene, o-dichlorobenzene, cyclohexane, and ethyl cyclohexane.

4. The method according to claim 1, wherein the gate insulating film and the organic semiconductor film are formed by forming an organic insulating film on the gate electrode, and applying the raw material solution onto the organic insulating film.

5. The method according to claim 1, wherein the polymer is at least one of poly(α-methylstyrene) and cycloolefin copolymer.

6. An organic transistor comprising:
  a gate insulating film and an organic semiconductor film collectively formed by applying, onto a gate electrode disposed on a base substrate, a raw material solution, in a film shape, including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7,
  the gate insulating film and the organic semiconductor film being formed on the gate insulating film by spontaneous phase separation; and
  a source electrode and a drain electrode disposed on the organic semiconductor film

[Chem. 18]

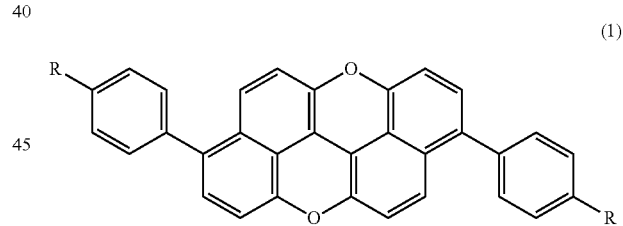

(1)

(where R is a linear or branched alkyl group)

[Chem. 19]

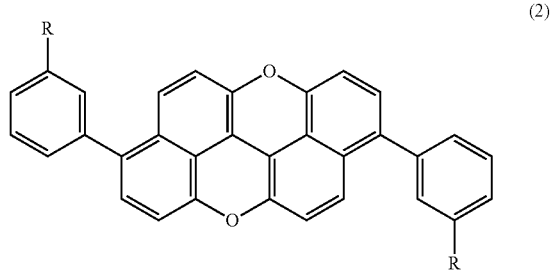

(2)

(where R is a linear or branched alkyl group)

[Chem. 20]

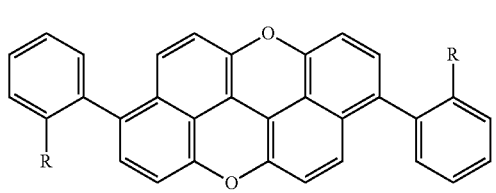

(3)

(where R is a linear or branched alkyl group)

[Chem. 21]

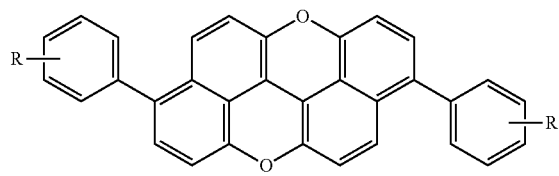

(4)

(where R is an alkyl group, a number of R's is 2 to 5)

[Chem. 22]

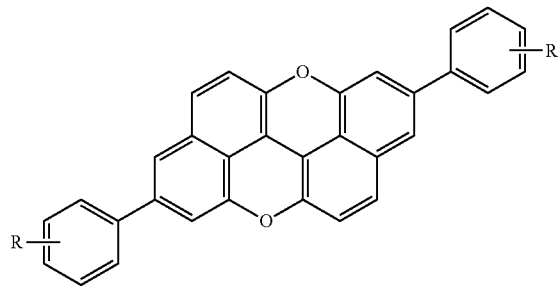

(5)

(where R is an alkyl group, a number of R's is 1 to 5)

[Chem. 23]

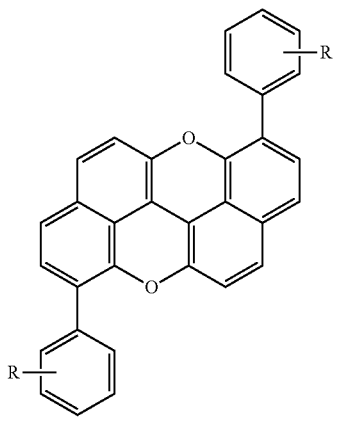

(6)

(where R is an alkyl group, and a number of R's is 1 to 5)

[Chem. 24]

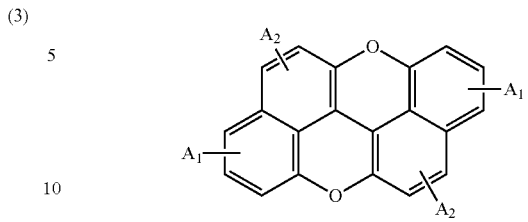

(7)

(where A1 and A2 are represented by Formula 8)

[Chem. 25]

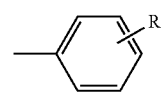

(8)

(where R is an alkyl group or another substituent, and a number of R's is 1 to 5).

7. The organic transistor according to claim 6, wherein the gate insulating film and the organic semiconductor film are formed by forming an organic insulating film on the gate electrode, and applying the raw material solution onto the organic insulating film.

8. The organic transistor according to claim 6, wherein the polymer is at least one of poly(α-methylstyrene) and cycloolefin copolymer.

9. An electronic apparatus comprising:
an organic transistor which includes a gate insulating film and an organic semiconductor film collectively formed by applying, onto a gate electrode disposed on a base substrate, a raw material solution, in a film shape, including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7,
the gate insulating film and the organic semiconductor film being formed on the gate insulating film by spontaneous phase separation, and
a source electrode and a drain electrode disposed on the organic semiconductor film

[Chem. 26]

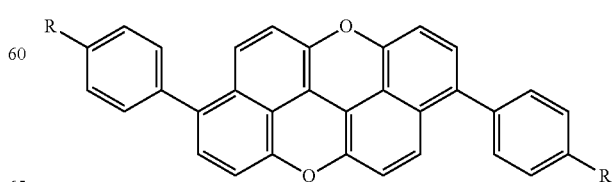

(1)

(where R is a linear or branched alkyl group)

[Chem. 27]

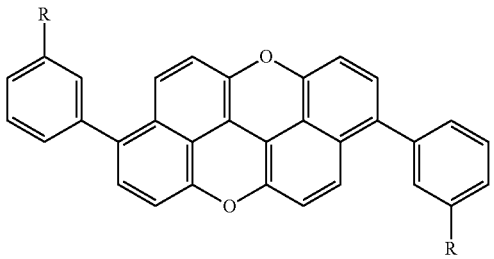

(2)

(where R is a linear or branched alkyl group)

[Chem. 28]

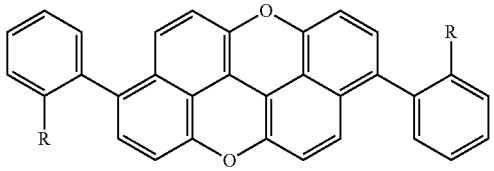

(3)

(where R is a linear or branched alkyl group)

[Chem. 29]

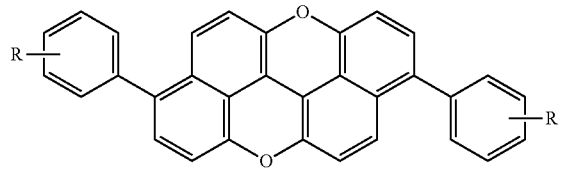

(4)

(where R is an alkyl group, and a number of R's is 2 to 5)

[Chem. 30]

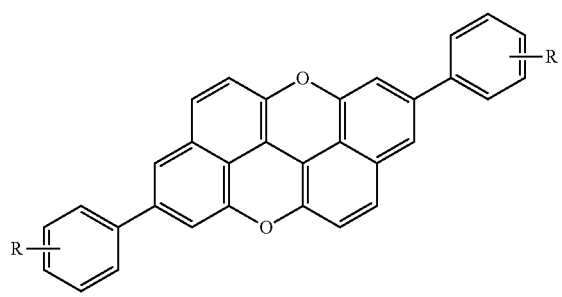

(5)

(where R is an alkyl group, and a number of R's is 1 to 5)

[Chem. 31]

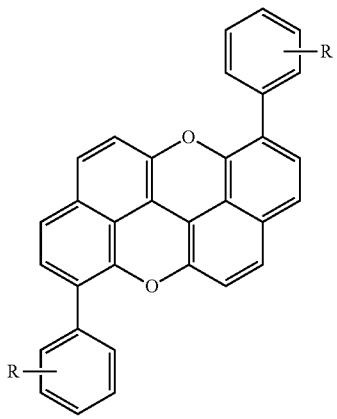

(6)

(where R is an alkyl group, a number of R's is 1 to 5)

[Chem. 32]

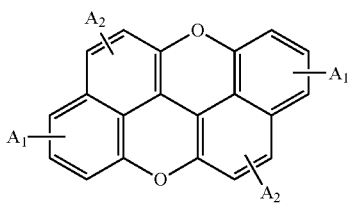

(7)

(where A1 and A2 are represented by Formula 8)

[Chem. 33]

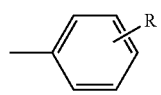

(8)

(where R is an alkyl group or another substituent, and a number of R's is 1 to 5).

10. A method of producing a semiconductor device, the method comprising:
collectively forming a gate insulating film and an organic semiconductor film by applying, onto a base substrate, a raw material solution, in a film shape, including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7,
the gate insulating film and the organic semiconductor film formed on the gate insulating film by spontaneous phase separation

[Chem. 34]

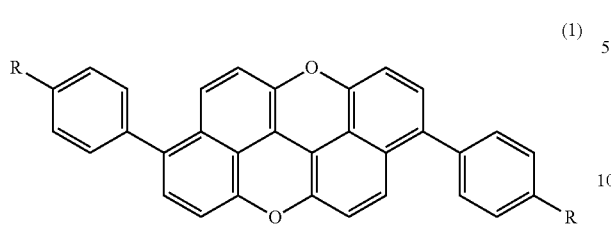
(1)

(where R is a linear or branched alkyl group)

[Chem. 35]

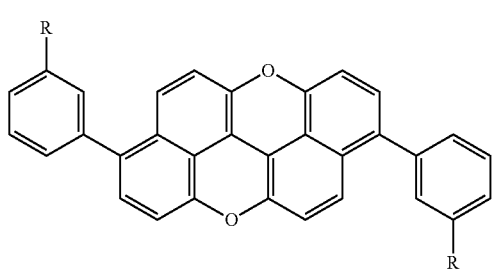
(2)

(where R is a linear or branched alkyl group)

[Chem. 36]

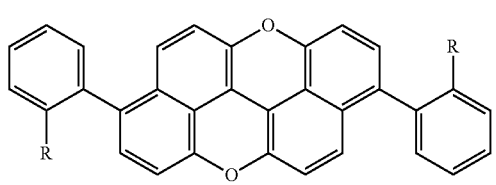
(3)

(where R is a linear or branched alkyl group)

[Chem. 37]

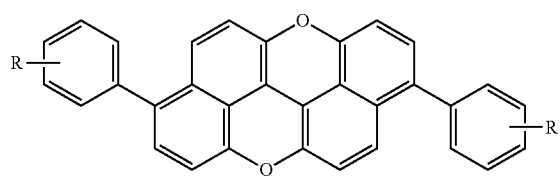
(4)

(where R is an alkyl group, a number of R's is 2 to 5)

[Chem. 38]

(5)

(where R is an alkyl group, a number of R's is 1 to 5)

[Chem. 39]

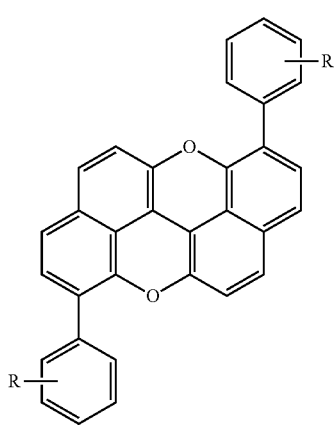
(6)

(where R is an alkyl group, and a number of R's is 1 to 5)

[Chem. 40]

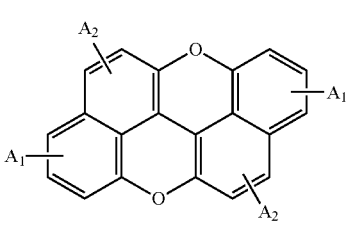
(7)

(where A1 and A2 are represented by Formula 8)

[Chem. 41]

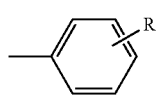
(8)

(where R is an alkyl group or another substituent, and a number of R's is 1 to 5).

11. A semiconductor device comprising:
a gate insulating film and an organic semiconductor film collectively formed by applying, onto a base substrate, a raw material solution, in a film shape, including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7, the gate insulating film and the organic semiconductor film being formed on the gate insulating film by spontaneous phase separation

[Chem. 42]

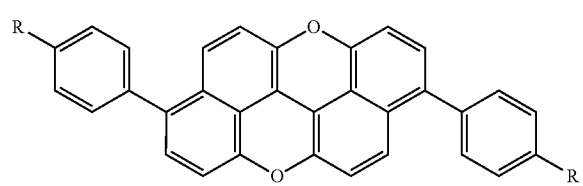

(1)

(where R is a linear or branched alkyl group)

[Chem. 43]

(2)

(where R is a linear or branched alkyl group)

[Chem. 44]

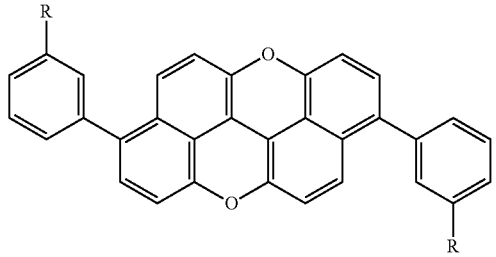

(3)

(where R is a linear or branched alkyl group)

[Chem. 45]

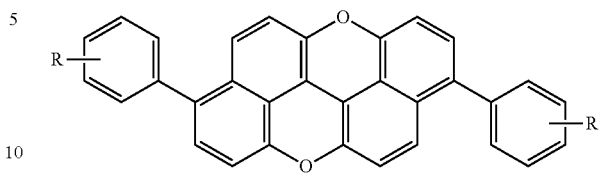

(4)

(where R is an alkyl group, a number of R's is 2 to 5)

[Chem. 46]

(5)

(where R is an alkyl group, and a number of R's is 1 to 5)

[Chem. 47]

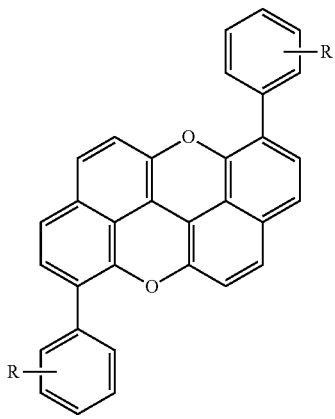

(6)

(where R is an alkyl group and a number of R's is 1 to 5)

[Chem. 48]

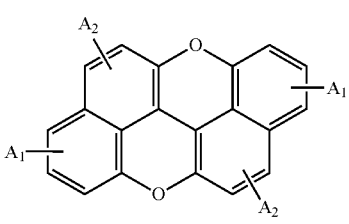

(7)

(where A1 and A2 are represented by Formula 8)

[Chem. 49]

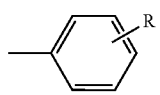
(8)

(where R is an alkyl group or another substituent, and a number of R's is 1 to 5).

12. An electronic apparatus comprising:
a semiconductor device which includes a gate insulating film and an organic semiconductor film collectively formed by applying, onto a base substrate, a raw material solution, in a film shape, including a polymer and at least one compound of a compound represented by General Formula 1, a compound represented by General Formula 2, a compound represented by General Formula 3, a compound represented by General Formula 4, a compound having a structure represented by General Formula 4, in which R is a substituent other than an alkyl group, a compound represented by General Formula 5, a compound represented by General Formula 6, a compound having a structure represented by General Formula 5 or 6, in which R is a substituent other than an alkyl group, and a compound represented by General Formula 7,
the gate insulating film and the organic semiconductor film formed on the insulating film by spontaneous phase separation

[Chem. 50]

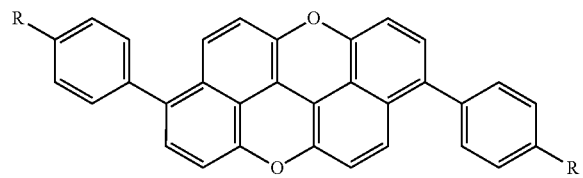
(1)

(where R is a linear or branched alkyl group)

[Chem. 51]

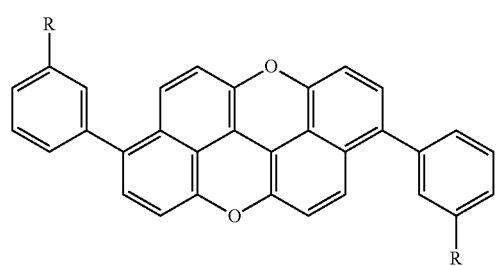
(2)

(where R is a linear or branched alkyl group)

[Chem. 52]

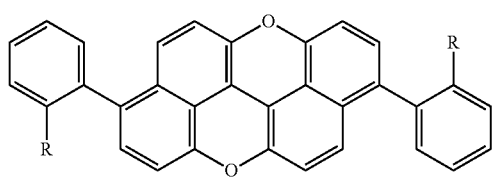
(3)

(where R is a linear or branched alkyl group)

[Chem. 53]

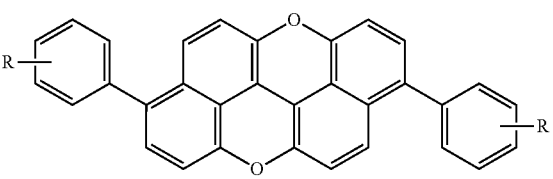
(4)

(where R is an alkyl group, and a number of R's is 2 to 5)

[Chem. 54]

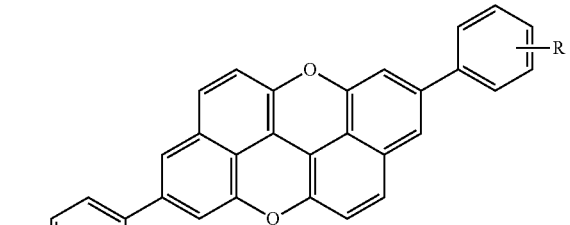
(5)

(where R is an alkyl group, and a number of R's is 1 to 5)

[Chem. 55]

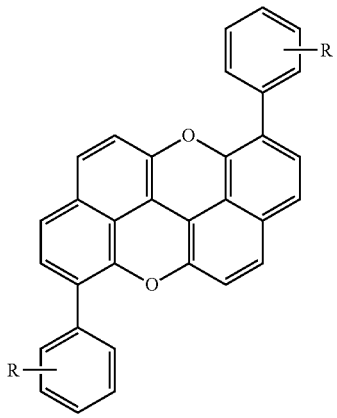
(6)

(where R is an alkyl group, and a number of R's is 1 to 5)

[Chem. 56]
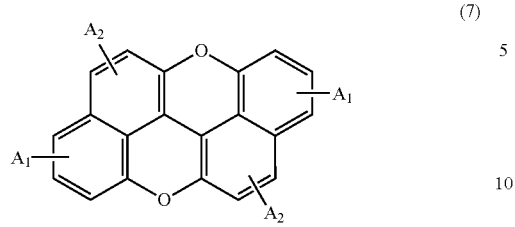
(7)
(where A1 and A2 are represented by Formula 8)
[Chem. 57]
(8)
(where R is an alkyl group or another substituent, and a number of R's is 1 to 5).
* * * * *